United States Patent [19]

Doyle, Jr. et al.

[11] 4,084,956

[45] Apr. 18, 1978

[54] BARBAN FORMULATION

[75] Inventors: William C. Doyle, Jr., Leawood; Marion F. Botts, Merriam, both of Kans.

[73] Assignee: Gulf Oil Corporation, Pittsburgh, Pa.

[21] Appl. No.: 819,807

[22] Filed: Jul. 28, 1977

Related U.S. Application Data

[63] Continuation-in-part of Ser. No. 697,585, Jun. 18, 1976, abandoned.

[51] Int. Cl.² ............................................. A01N 9/20
[52] U.S. Cl. ................................. 71/111; 71/DIG. 1
[58] Field of Search ........................... 71/DIG. 1, 111

[56] References Cited

U.S. PATENT DOCUMENTS 3,253,904  5/1966  Harrison ..................... 71/111 X

FOREIGN PATENT DOCUMENTS 1,323,697  7/1973  United Kingdom ............. 71/111
1,420,072  1/1976  United Kingdom ............. 71/111

Primary Examiner—Joseph Paul Brust
Attorney, Agent, or Firm—Carl A. Cline

[57] ABSTRACT

Barban (4-chloro-2-butynyl m-chlorocarbanilate) is formulated as liquid emulsifiable concentrates containing as much as twenty to thirty percent of the herbicide which have improved efficacy and unlike other formulations of higher concentration, are also safe to use in wheat fields. A particularly critical component of the improved concentrate is a condensation product of $C_{12}$ to $C_{18}$ fatty alcohols with from ten to forty units of ethylene oxide.

3 Claims, No Drawings

BARBAN FORMULATION

This application is a continuation-in-part of U.S. Pat. application Ser. No. 697,585 filed June 18, 1976, now abandoned.

DESCRIPTION OF THE INVENTION

A. BACKGROUND

Barban is a herbicide which has been employed for several years to control wild oats in agriculture in the cool temperate zones of the earth in crops such as wheat, barley, rape and sugar beets. Conventional formulations in the past have been emulsifiable liquid concentrates containing about one pound of active material per gallon (about 0.12 kg per liter). From the standpoint of volume and weight considerations in packaging and shipping, it is desirable to formulate barban in much more concentrated form. However, the selectivity of barban, particularly as between wild oats and wheat, is barely adequate and the use of more efficient solvents and solubilizers for barban usually has a deleterious effect. The loss of selectivity is usually accompanied by an increase in activity. However, the overall result is a net decrease in utility. By way of illustration, in British patent 1 323 697 there is disclosed a formulation comprising (a) 10 to 30% by weight barban; (b) 10 to 30 % by weight condensate of $C_8$ to $C_{16}$ fatty alcohol with 2 to 6 moles of ethylene oxide; (c) 2 to 15% by weight emulsifier and (d) 25 to 75% by weight hydrocarbon oil comprising an aromatic hydrocarbon solvent. The compositions of the patent have higher barban concentration than the old formulations, along with good efficacy. However, they are unsafe for wild oats control in wheat and use must be limited to crops such as barley, rape and sugar beets. The solubility characteristics of technical barban continue to present a difficult formulation problem. Until the present time the principal application of barban, in combating wild oats in wheat fields, is still practiced with the use of conventional one pound per gallon emulsifiable concentrate.

B. SUMMARY OF THE INVENTION

Briefly, we have invented emulsifiable concentrates which contain 20 to 30 percent barban and which have both high efficacy on wild oats and safety on wheat. These formulations comprise by weight:

(a) 20 to 30% barban, preferably 20 to 26%;
(b) 5 to 25%, preferably 5 to 10% of a condensation product of $C_{12}$ to $C_{18}$ fatty alcohols with 10 to 40 units of ethylene oxide. (Preferably about $C_{16}$ fatty alcohols are condensed with an average ratio of 20 units of ethylene oxide);
(c) at least 0.5 parts, preferably from 1.5 to 2.5 parts per part of component (b) of an emulsifier, which is preferably a blend of non-ionic and anionic surfactants, selected for ability to emulsify barban; and
(d) the balance being a solvent comprising a major proportion of alkylbenzenes or alkylnaphthalenes along with other hydrocarbons within or above kerosene boiling range.

C. DETAILED DESCRIPTION

We have discovered that the fatty alcohol-ethylene oxide condensation products employed as surface active agents to aid in obtaining homogeneous emulsifiable concentrates of barban have a critical effect on barban selectivity. Whereas prior art formulations have employed fluid-type polyoxyethylene condensation products, the substances employed in our improved formulations are waxy solids at room temperature. This component of the formulations appears to be responsible for a differential enhancement of efficacy which increases selectivity so as to make possible the improvement of control of wild oats while decreasing the injury to wheat. Manufacture of the alcohol-ethylene oxide condensation products, commonly called polyoxyethylene alcohols is described in Chapter 4 pages 86–132 of "Nonionic Surfactants" edited by Martin J. Schick, published by Marcel Dekker, Inc., New York, 1967. These surface-active agents are articles of commerce, available from several sources.

The exact nature of the organic solvent used in these improved formulations appears not to be critical. Those which have been used successfully include several representatives of three classes of commercial mixed aromatic solvents, (see Table 1) the mixed $C_9$ fraction having a boiling range of about 315°–350° F, the mixed $C_{10}$ fractions having a boiling range of about 350°–425° F, and the heavy aromatic naphthas with a boiling range about 400°–600° F.

The heavy aromatic naphtha type solvents are mixtures of naphthalene and methyl substituted naphthalene boiling in the range of approximately 400°–600° F.

Though hydrocarbon solvents, particularly the mixed $C_{10}$ aromatic fractions are preferred as the major solvent component from the standpoints of cost and efficacy, varying amounts of other solvents may also be included - ketones such as isophorone, cyclohexanone or mesityl oxide; esters such as amyl acetate and chlorinated hydrocarbons such as chlorobenzene or 1,2-dichloroethane.

TABLE I

| Suitable Commercial Mixed Aromatic Solvents | | |
|---|---|---|
| Solvent Trade Name | Fraction | Commercial Source |
| Aromatic 100 | $C_9$ | Exxon Corp. |
| Super Hi Flash Naphtha | $C_9$ | Union Oil Co. |
| Tenneco 500-100 | $C_9$ | Tenneco Oil Co. |
| Aromatic 150 | $C_{10}$ | Exxon Corp. |
| Solvent 145 | $C_{10}$ | Sun Oil Co. |
| Amsco Solv. G | $C_{10}$ | Union Oil Co. |
| Amsco Solv. E98 | heavy aromatic naphtha | Union Oil Co. |
| Sure Sol 180 | heavy aromatic naphtha | Sun Oil Co. |
| Hi Sol 4-5-T | heavy aromatic naphtha | Ashland Oil Co. |

The emulsifier may be selected from commercial products which are sold for use in herbicide formulations. Commercial emulsifiers which give satisfactory results, for example, are blends of anionic and nonionic surfactants, one of which has been sold by Retzloff Chemical Co. under the trade name Sponto ("W" in tables 2 and 3) and others are available under the trade name Atlox from Atlas Chemical Industries ("A" in tables 2 and 3). Other emulsifiers of the general type are available from other sources. Selection will commonly be made by testing emulsifier efficiency and comparing costs. In general, the emulsifier functions to produce good aqueous dispersions upon mixing of the formulations in water and has no significant beneficial effect on efficacy of barban. The function of the polyoxyethylene alcohols in the past has been to keep both barban and the emulsifier in solution. Since these products were in effect, being used as co-solvents, the liquid products represented a natural choice. It was not previously known that the polyoxyethylene alcohols have a significant effect on entry or transport of barban in plants and the heavier waxy condensation products were not employed in barban formulations.

A number of emulsifiable concentrate formulations were prepared according to three general recipes, with variation of fatty alcohol-ethylene oxide composition and hydrocarbon solvent as disclosed below. Percentages of components in formulations are by weight. All formulations were compared against a commercial one pound per gallon formulation which is commonly used to control wild oats in wheat. The application levels were chosen so as to render observable phytotoxicity effects both greater and less than that of the standard formulation, which was rated at 100 percent. The results are tabulated below in tables 2, 3 and 4.

TABLE 2

Results of Phytotoxicity Tests of General Formulation
24% Barban
5.3% Fatty Alcohol/Ethylene oxide condensate
16% Anionic - nonionic surfactant blend (Sponto)
made up to 100% with Aromatic hydrocarbon solvent

| Formulation No. | Fatty Alcohol/ETO Condensate | | | Phytotoxicity (% of Standard) | |
|---|---|---|---|---|---|
| | Alcohol | Mols ETO (Average) | Solvent | Wild Oats (2 oz/a) | Wheat (1 lb/A) |
| 142 | Cetyl ($C_{16}$) | 20 | Aromatic 100 | 100 | 35 |
| 143 | Cetyl | 20 | Aromatic 150 | 71 | 65 |
| 144 | Cetyl | 20 | Super Hi Flash naphtha | 100 | 15 |
| 150 | Stearyl ($C_{18}$) | 20 | Aromatic 100 | 52 | 233 |
| 151 | Stearyl | 40 | Aromatic 100 | 48 | 100 |
| 152 | Lauryl ($C_{12}$) | 23 | Aromatic 100 | 91 | 100 |
| 153 | Oleyl ($C_{18}$) | 20 | Aromatic 100 | 59 | 233 |
| 175 | Cetyl | 20 | Solvent 145 | 106 | 0 |
| Commercial formulation according to British Patent 1 323 697. (average of 5 tests) | | | | 93 | 383 |

TABLE 3

Results of Phytotoxicity Tests of General Formulation
23% Barban
9% Fatty alcohol/ethylene oxide condensate
21% Anionic - nonionic surfactant blend (Sponto or Atlox)
made up to 100% with Aromatic hydrocarbon solvent

| Formulation No. | Fatty Alcohol/ETO Condensate | | Surfactant Blend | Solvent | Phytotoxicity (% of Standard) | |
|---|---|---|---|---|---|---|
| | Alcohol | Mols ETO (Average) | | | Wild Oats (2 oz/A) | Wheat (1 lb/A) |
| 159 | Cetyl ($C_{16}$) | 20 | W | Amsco Solv G | 119 | 0 |
| 160 | Cetyl | 20 | W | Solvent 145 | 124 | 0 |
| 161 | Cetyl | 20 | W | Tenneco 500-100 | 96 | 0 |
| 162 | Cetyl | 20 | W | Super Hi Flash Naphtha | 100 | 0 |
| 177 | Cetyl | 20 | A | Solvent 145 | 100 | 100 |
| 178 | Cetyl | 20 | A | Tenneco 500-100 | 92 | 77 |
| 179 | Cetyl | 20 | A | Super Hi Flash Naphtha | 86 | 100 |
| 220 | Cetyl | 20 | W | Sure Sol 180 | 133 | 50 |
| 172 | Cetyl | 20 | W | Amsco Solv E 98 | 94 | 0 |
| Commercial formulation according to British Patent 1 323 697. (Average of 5 tests) | | | | | 93 | 383 |
| 216 | Cetyl | 20 | A | Amsco Solv G | 42 | 6 |
| 223 | Cetyl | 20 | A | Amsco E 98 | 67 | 10 |
| 222 | Cetyl | 20 | W | 92% Sure Sol 180 with 8% amyl acetate | 58 | 10 |

TABLE 4

Results of Phytotoxicity Tests of General Formulation
23% Barban
12% Fatty alcohol/ethylene oxide condensate
18% Anionic-nonionic surfactant blend (Sponto or Atlox)
made up to 100% with Aromatic hydrocarbon solvent

| Formulation No. | Fatty Alcohol/ETO Condensate | | Surfactant Blend | Solvent | Phytotoxicity (% of Standard) | |
|---|---|---|---|---|---|---|
| | Alcohol | Mols ETO | | | Wild Oats (2 oz/A) | Wheat (1 lb/A) |
| 217 | Cetyl ($C_{16}$) | 20 | W | Amsco Solv G | 118 | 23 |
| 221 | Cetyl | 20 | W | Sure Sol 180 | 118 | 23 |
| 224 | Cetyl | 20 | A | Amsco Solv E98 | 118 | 23 |

TABLE 4-continued

Results of Phytotoxicity Tests of General Formulation
23% Barban
12% Fatty alcohol/ethylene oxide condensate
18% Anionic-nonionic surfactant blend (Sponto or Atlox)
made up to 100% with Aromatic hydrocarbon solvent

| Formulation No. | Fatty Alcohol/ETO Condensate Alcohol | Mols ETO | Surfactant Blend | Solvent | Phytotoxicity (% of Standard) | |
|---|---|---|---|---|---|---|
| | | | | | Wild Oats (2 oz/A) | Wheat (1 lb/A) |
| 207 | Cetyl | 20 | W | Hi Sol 4-5-T | 100 | 0 |
| 218 | Cetyl | 20 | W | 8% Amyl Acetate 92% Amsco Solv G | 108 | 13 |

Study of these tabulated results reveals that better results are obtained with use of the condensation product of $C_{16}$ alcohol with about 20 mols of ethylene oxide. The $C_{18}$ alcohol condensation products cause less injury to wheat at the higher end of the range of ethylene oxide units in the molecule. The $C_{12}$ alcohol condensation products appear to give performance approaching the standard. In Table 3, in particular, it is seen that with use of larger proportions of alcohol-ethylene oxide condensation product and emulsifier, performance may be made to exceed that of the standard formulation, both with respect to wild oat control and injury to wheat. Some differences will be observed in various combinations of hydrocarbon solvents and emulsifiers. These differences are not large when one considers the wide variation in chemical composition of these two components of the improved formulations. It is well within the skill of the ordinary worker to judge which of these purchased components work best together. Because the quality of solvents is known to vary, it is common practice to make routine tests of individual batches of these materials. Performance of solvents in combination with selected emulsifiers may be readily evaluated in a routine manner. By using the data of Tables 2, 3 and 4 as a guide, a skilled worker in the art will be enabled to prepare emulsifiable concentrates containing more than twenty percent technical barban which are at least as effective as standard formulations on wild oats and which have improved safety on wheat. It will be understood that when percents by weight in the formulations are specified in whole numbers that some variation from these percentages will occur during formulation and is permissible, particularly if the error is less than plus or minus one percent.

Various formulations of those tabulated above have been prepared in substantial quantities and used in various locations to control wild oats in wheat. For example, Formulation No. 223 of Table 3 was prepared and evaluated in the field, having the following makeup when in the containers and ready for use:

| Component | Percent by wt. |
|---|---|
| Barban | 22.4 |
| Cetyl alcohol-ethylene oxide condensation product | 9 |
| Anionic-nonionic surfactant blend | 21 |
| Dye for identification | 0.1 |
| Heavy aromatic naphtha | Balance of formulation |

Specific gravity 1.073, homogeneous in appearance.

This formulation exhibited a high level of wild oat control when applied at rates of both 4 oz. and 8 oz. of barban per acre, without significant injury to wheat or barley. The formulation was stable in storage over a wide temperature range and formed an aqueous dispersion with water which sprayed freely, without plugging spray nozzles. As compared with the standard formulation, containers of the new composition occupied only about half the space and weighed about half as much.

We claim:

1. A selectively herbicidal composition which comprises, by weight,
    (a) 20 to 30 percent barban, as the sole herbicidal agent,
    (b) 5 to 25 percent of a waxy solid condensation product of $C_{12}$ to $C_{18}$ fatty alcohols with 10 to 40 units of ethylene oxide
    (c) at least 0.5 parts per part of component (b) of an emulsifier, selected for ability to emulsify barban, and
    (d) the balance a solvent comprising a major proportion of alkylbenzenes or alkylnaphthalenes along with a minor proportion of other hydrocarbons within or above kerosene boiling range.

2. A selectively herbicidal composition which comprises, by weight,
    (a) 20 to 26 percent barban, as the sole herbicidal agent,
    (b) 5 to 10 percent of a waxy solid condensation product of $C_{16}$ fatty alcohols with an average of about 20 units of ethylene oxide,
    (c) from 1.5 to 2.5 parts, per part of component (b) of an emulsifier which is a blend of anionic and nonionic surfactants, selected for ability to emulsify barban, and
    (d) the balance a solvent comprising a major proportion of alkylbenzenes or alkylnaphthalenes along with a minor proportion of other hydrocarbons within or above kerosene boiling range.

3. A selectively herbicidal composition which comprises by weight,
    (a) 22 to 23 percent barban, as the sole herbicidal agent,
    (b) about 9 percent of a waxy solid condensation product of $C_{16}$ fatty alcohols with an average of about 20 units of ethylene oxide,
    (c) about 21 parts of an emulsifier which is a blend of anionic and nonionic surfactants, selected for ability to emulsify barban, and
    (d) about 47 percent of a heavy aromatic naphtha as a solvent for components (a), (b) and (c).

* * * * *